United States Patent [19]
Wilk

[11] Patent Number: 5,437,278
[45] Date of Patent: Aug. 1, 1995

[54] MEDICAL DIAGNOSIS SYSTEM AND METHOD

[76] Inventor: Peter J. Wilk, 185 West End Ave., New York, N.Y. 10023

[21] Appl. No.: 819,120

[22] Filed: Jan. 10, 1992

[51] Int. Cl.⁶ .............................................. A61B 5/00
[52] U.S. Cl. ............................ 128/653.1; 128/653.2; 128/660.07; 128/630; 364/413.02; 364/413.13
[58] Field of Search ............ 128/653.1, 653.2, 660.07, 128/664, 665, 734, 736, 413.02, 413.13, 413.14, 630, 672

[56] References Cited

U.S. PATENT DOCUMENTS

| | | | |
|---|---|---|---|
| 4,437,161 | 5/1984 | Anderson . | |
| 4,641,349 | 2/1987 | Flom et al. . | |
| 4,667,335 | 5/1987 | Deindoerfer . | |
| 4,697,594 | 10/1987 | Mayo, Jr. | 128/653.1 |
| 4,767,717 | 8/1988 | Baisden | 128/653.1 |
| 4,838,681 | 6/1989 | Pavlidis . | |
| 4,839,822 | 6/1989 | Dormond et al. . | |
| 4,947,245 | 8/1990 | Ogawa et al. . | |
| 4,951,653 | 8/1990 | Fry et al. | 128/653.1 |
| 4,951,674 | 8/1990 | Zanakis et al. | 128/653.1 |
| 4,989,083 | 1/1991 | Eino . | |
| 5,027,817 | 7/1991 | John | 128/653.1 |
| 5,099,844 | 3/1992 | Faupel | 128/734 |
| 5,099,846 | 3/1992 | Hardy | 128/653.1 |
| 5,140,988 | 8/1992 | Stouffer et al. . | |

FOREIGN PATENT DOCUMENTS

| | | |
|---|---|---|
| 21647711 | 3/1986 | United Kingdom . |
| 9107135 | 5/1991 | WIPO . |

Primary Examiner—Krista M. Pfaffle
Attorney, Agent, or Firm—R. Neil Sudol; Henry D. Coleman

[57] ABSTRACT

A medical diagnostic system comprises a monitoring device juxtaposable to a patient for collecting individualized medical data about the patient's condition, and a digitizer operatively connected to the monitoring device for digitizing the data. A computer is operatively connected to the digitizer and a memory which stores medical data for a multiplicity of previously diagnosed medical conditions. The computer is operated to compare digitized data about the patient's condition with the data stored in the memory and for deriving a diagnosis as to the patient's condition. The computer is connected to an ooutput device, e.g., a printer, for communicating the derived diagnosis to a user.

14 Claims, 4 Drawing Sheets

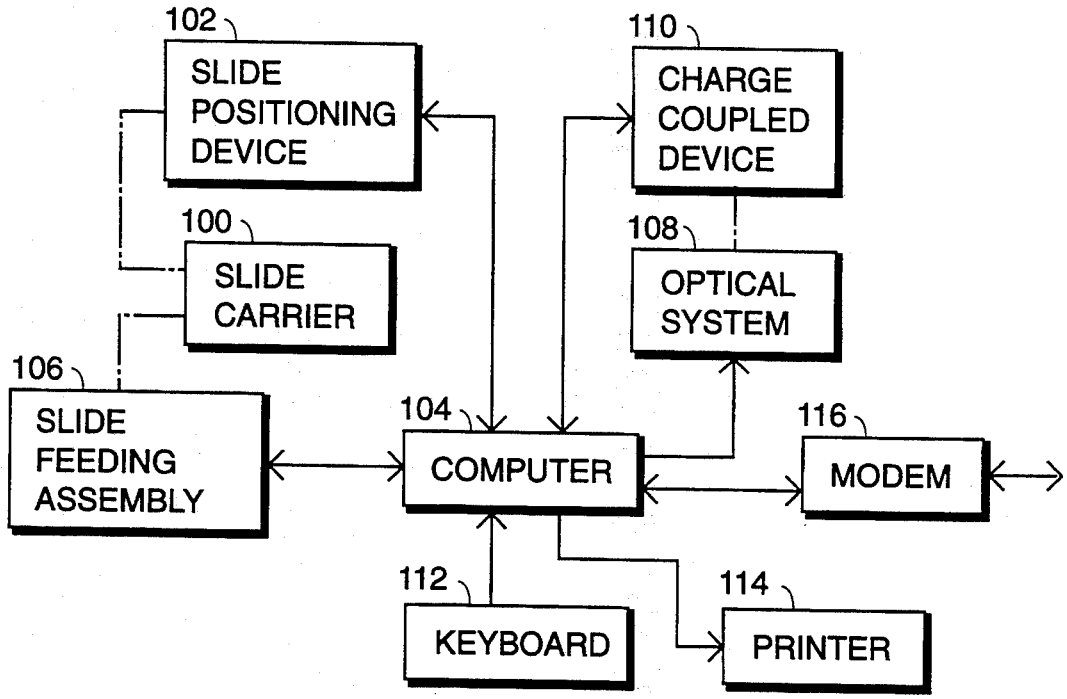
FIG. 5
FIG. 6
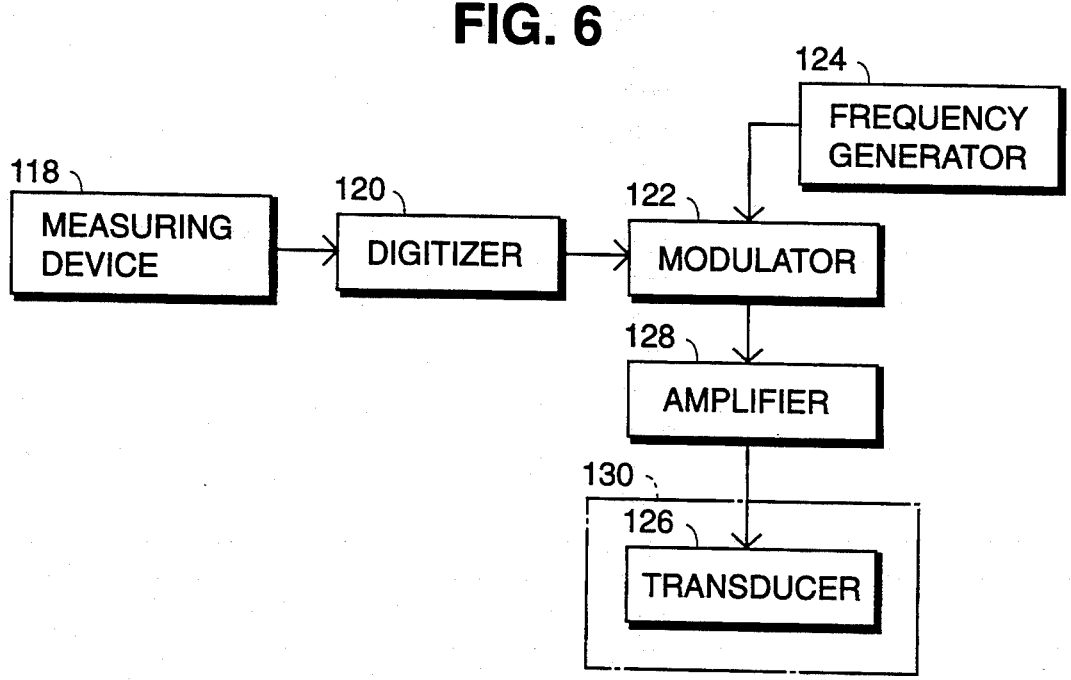
FIG. 7

MEDICAL DIAGNOSIS SYSTEM AND METHOD

BACKGROUND OF THE INVENTION

This invention relates to an automatic medical diagnostic system. This invention also relates to an associated diagnostic method.

Medical and hospitalization costs are ever increasing. In addition, the costs and the time needed to educate doctors continue to rise.

Medical testing, particularly the testing of blood, urine and other specimens, has long been a specialized practice relegated to laboratories. This centralization reduces costs in part because of the benefits of mass production, assembly line techniques, and automation. Specialized labaoratories possess skills and information which isolated doctors and even entire hospitals may lack.

OBJECTS OF THE INVENTION

An object of the present invention is to provide a medical diagnostic system and a related diagnostic method.

A more particular object of the present invention is to provide such a diagnostic system and method which reduces medical diagnosis costs.

Another particular object of the present invention is to provide such a diagnostic system and method which can be used by persons having less training than traditional physicians.

A further particular object of the present invention is to provide an at least partially automated diagnostic system and method.

Another object of the present invention is to provide an automated diagnostic system which utilizes centralization to provide the benefits of large amounts of information and data processing capacity.

Another, more particular, object of the present invention is to provide an automated medical diagnostic system which utilizes image type information.

A further particular object of the present invention is to provide a medical diagnostic system wherein diagnoses are made by computer.

Yet another particular object of the present invention is to provide such a diagnostic system wherein the computer is centralized.

SUMMARY OF THE INVENTION

A medical diagnostic system comprises, in accordance with the present invention, a monitoring device juxtaposable to a patient for collecting individualized medical data about the patient's condition, and a digitizer operatively connected to the monitoring device for digitizing the data. A computer is operatively connected to the digitizer and to a memory which stores medical data for a multiplicity of previously diagnosed medical conditions. The computer is operated to compare digitized data about the patient's condition with the data stored in the memory and to derive a diagnosis as to the patient's condition. The computer is connected to an output device, e.g., a printer, for communicating the derived diagnosis to a user.

Pursuant to another feature of the present invention, the monitoring device includes a scanner for generating in electrically encoded form a visually readable image of an organic part of the patient. An analyzing device may be operatively connected to the scanner for determining from the image a value of at least one organic parameter pertaining to the patient.

In accordance with the present invention, the scanner may take the form, for example, of an MRI apparatus, a CAT scanner, an X-ray machine, an ultrasonography apparatus, or a video camera with or without magnification optics for magnifying a sample on a slide.

Pursuant to another feature of the present invention, the monitoring device includes a measuring device for measuring a predetermined physiological parameter of the patient. The measuring device may take the form, for instance, of an electronic thermometer, an electronic blood pressure gauge, a pulmonary function apparatus, a doppler study apparatus, an EEG machine, an EKG machine, an EMG machine, or a pressure measurement device.

A medical diagnostic system comprises, in accordance with a specific embodiment of the present invention, (a) a scanner for generating in electrically encoded form a visually readable image of an organic part of the patient, (b) an analyzing device operatively connected to the scanner for determining from the image a value of at least one organic parameter pertaining to the patient, (c) a memory for storing a plurality of previously measured values for each of a multiplicity of predetermined organic parameters, (d) a computer operatively connected to the memory and the analyzing device for comparing the value of the one organic parameter with a plurality of values stored in the memory and for deriving a diagnosis as to the patient's condition, and (e) an output device operatively connected to the computer for communicating the derived diagnosis to a user.

The parameterization of the images enables storage of previously obtained medical data of the same kind in a local computer. For example, in the event that the image system is video used, for example, in dermatological diagnosis, an image of a skin surface of a patient is analyzed to derive such parameters as percentage of skin covered by abnormal condition, the range of sizes of individual ulcers, the range of color variation (e.g., whether bleeding is symptomatic). These parameters represent a distillation of the total information content and accordingly require a substantially reduced storage space.

However, it is within the contemplation of the instant invention that the memory stores entire images related to different diseases. For example, images of skin conditions are stored at a dermatological diagnosis and treatment facility. The computer compares the image of a patient with the previously stored images, for example, by breaking down the current image into sections and overlaying the sections with sections of the stored images, at variable magnification levels. A combination of a parameterization technique and an image overlay technique is considered optimal.

A medical diagnostic system comprises, in accordance with another specific embodiment of the present invention, (a) a measuring device for measuring a predetermined physiological parameter of a patient and for generating a digital signal codifying a magnitude of the parameter, (b) a memory for storing medical data for a multiplicity of previously diagnosed medical conditions, (c) a computer operatively connected to the memory and the measuring device for comparing the magnitude, as encoded in the digital signal, with data stored in the memory and for deriving a diagnosis as to the patient's condition, and (d) an output device operatively connected to the computer for communicating the derived diagnosis to a user.

The measuring device is designed to monitor and quantify a predetermined biological or physiological parameter, such as temperature, blood pressure, muscle contraction strength (e.g. colonic, esophogeal), respiration volume or effectiveness, the rate of blood flow, electrical voltages (brain, heart, muscle), etc.

Pursuant to another feature of the present invention, the computer is a remote, central computer. The measured and digitized biological or physiological parameter is transmitted via a telephone line linkage to the computer, which transmits a diagnosis in electrically encoded form back to a printer or other output device at the diagnosis station.

Alternatively, the diagnosis may be implemented by a local computer disposed at the location that the parameter measurement takes place. The local computer may be connected additionally to a central computer, the diagnosis being performed by the central computer and communication therewith being mediated by the local computer.

A medical diagnostic method in accordance with the present invention comprises the steps of (i) at least partially automatically monitoring a patient to collect individualized medical data about the patient's condition, (ii) generating a digitized signal encoding the data, (iii) automatically comparing the digitized data about the patient's condition with data stored in an electronic memory to derive a diagnosis as to the patient's condition, and (iv) communicating the derived diagnosis to a user.

Pursuant to another feature of the present invention, the step of monitoring includes the step of scanning the patient to generate in electrically encoded form a visually readable image of an organic part of the patient.

Pursuant to an alternative or additional feature of the present invention, the step of monitoring includes the step of at least partially automatically measuring a predetermined physiological parameter of the patient.

Pursuant to a further feature of the present invention, the method also comprises the step of automatically analyzing the image to determine a value of at least one organic parameter pertaining to the patient.

A medical diagnostic system and a related diagnostic method in accordance with the present invention provide many benefits of automation. Large amounts of information are accessible for making each diagnosis on a patient. The feature of computer centralization provides for enhanced data processing capability. An automated medical diagnostic system in accordance with the present invention may utilize image type information. Such image processing is useful in making diagnoses from MR images, cat scanned X-ray images, ultrasonographic images and optical images (slides, video).

Because diagnoses are made by computer in accordance with the present invention, it is frequently unnecessary to have a doctor present during data taking (symptom recording and measurement) and communication of the diagnosis to the patient. Any assistance may be provided by relatively unskilled aides.

Even if the patient eventually sees a physician for confirming the diagnosis, the computer input will facilitate the physician's evaluation of the patient's condition and reduce the amount of time necessary for the physician to examine the patient.

Accordingly, a system and method in accordance with the present invention reduces expense and saves physician time.

BRIEF DESCRIPTION OF THE DRAWING

FIG. 5 is a diagram showing the composition of a data string or module used in the system of FIG. 4.

FIG. 6 is a block diagram of a computerized slide scanning system, in accordance with the present invention.

FIG. 7 is a block diagram of a device for measuring a diagnostic parameter and transmitting the measurement over the telephone lines.

DETAILED DESCRIPTION

Figure 1:
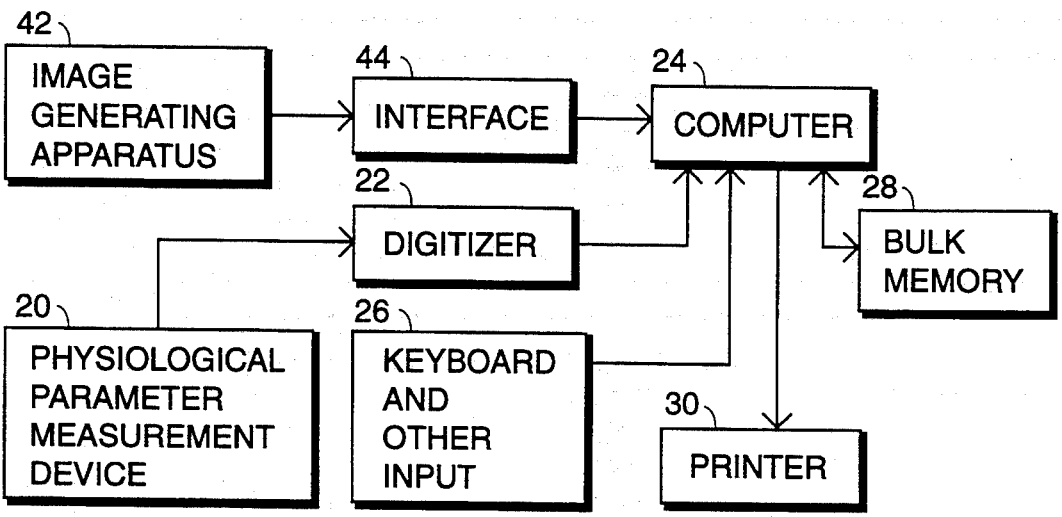
FIG. 1 is a block diagram of a medical diagnostic system, in accordance with the present invention.

As illustrated in FIG. 1, a medical diagnostic system comprises a device 20 for monitoring and measuring a biological or physiological parameter. Monitoring and measuring device 20 is juxtaposable to a patient for collecting individualized medical data about the patient's condition. Device 20 may take the form of an electronic thermometer, an electronic blood pressure gauge, a pulmonary function apparatus, a doppler study apparatus, an EEG machine, an EKG machine, an EMG machine, or a pressure measurement device, etc., or include a plurality of such components.

Monitoring and measuring device 20 is connected at an output to a digitizer 22 which converts normally analog type signals into coded binary pulses and transmits the resulting digital measurement signal to a computer 24. Digitizer 22 may be incorporated into a housing (not shown) enclosing all or part of the monitoring and measuring device 20. Moreover, digitizer 22 may be an integral part of monitoring and measuring device 20.

Computer 24 receives instructions and additional input from a keyboard 26. Keyboard 26 is used to feed computer 24 information for identifying the patient, for example, the patient's age, sex, weight, and known medical history and conditions. Such medical conditions may include past diseases and genetic predispositions.

Computer 24 is also connected to an external memory 28 and an output device 30 such as a printer or monitor. Memory 28 stores medical data for a multiplicity of previously diagnosed medical conditions which are detectable by analysis of data provided by monitoring and measuring device 20.

Figure 2:
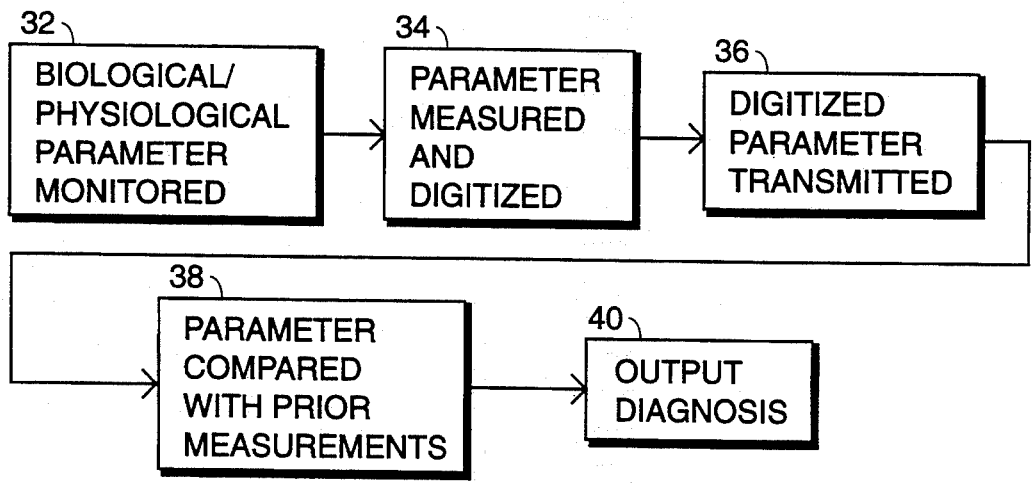
FIG. 2 is a flow-chart diagram illustrating steps in a mode of operation of the diagnostic system of FIG. 1.

As illustrated in FIG. 2, monitoring and measuring device 20 detects a magnitude of a predetermined biological or physiological parameter in a step 32. Digitizer 22 converts the detected magnitude into a pre-established digital format in a step 34 and transmits the digital signal to computer 24 in a step 36. Computer 24 is operated in a step 38 to compare the digitized data from monitoring and measuring device 20 with the data stored in memory 28 and to derive a diagnosis as to the patient's condition. The diagnosis is then communicated to the user (operator) and to the patient via output device 30 in a step 40.

If monitoring and measuring device 20 measures a physiological function characterized by a plurality of different variables, for example, the electric potential at different points on the patient's body (EEG, EKG, EMG), these variables may be broken down by computer 24 into one or more parameters, e.g., a frequency packet. The measured values of the pre-established parameters are then compared with parameter ranges stored in memory 28 for the type of parameter and the kind of patient, as characterized by sex, age, weight, etc. If the measured values of the pre-established parameters fall within expected ranges, as stored in memory 28, then computer 24 communicates a "normalcy" finding via printer 30. If, on the contrary, the measured values of one or more parameters fall outside the normal ranges, then a diagnosis of a possible medical condition is printed out.

As further illustrated in FIG. 1, the medical diagnostic system may comprise, in addition to or alternatively to monitoring and measuring device 20, an image generating apparatus or scanner 42 for generating in electrically encoded form a visually readable image of an organic part of the patient. Scanner 42 may take the form of an MRI apparatus, a CAT scanner, an X-ray machine, an ultrasonography apparatus, or a video camera with or without magnification optics for magnifying a sample on a slide. The video camera can be used for obtaining an image of a portion of a patient's skin.

Scanner 42 is connected via an interface 44 to computer 24.

Figure 3:
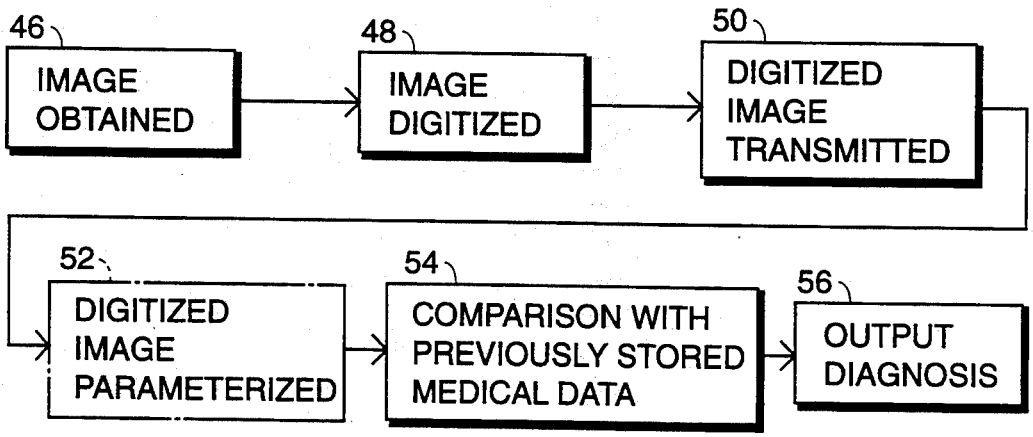
FIG. 3 is a flow-chart diagram illustrating steps in another mode of operation of the diagnostic system of FIG. 1.

As shown in FIG. 3, scanner 42 obtains an image of a tissue or organ in a step 46. The image is digitized, either by scanner 42 or interface 44 in a step 48, and is transmitted to computer 24 in a step 50. Computer 24 is operated in a step 52 to analyze the image from scanner 42 and determine specific values for a multiplicity of predetermined parameters. For example, in the event that scanner 42 takes the particular form of a video camera for dermatological diagnosis, an image of a skin surface of a patient is analyzed by computer 24 to derive such parameters as percentage of skin covered by abnormal condition, the range of sizes of individual ulcers, the range of color variation (e.g., whether bleeding is symptomatic).

The specific values of pre-established parameters calculated by computer 24 from electrically encoded images transmitted from scanner 42 are compared by computer 24 with previously determined parameter ranges stored in memory 28. For example, if a pregnant woman's fetus is being scanned by ultrasonography, the lengths of the fetal appendages, arms, legs, fingers, etc., are compared with each other and with respective fetal appendage ranges recorded in memory 28 for the stage of pregnancy, weight of the fetus, and possibly weight of the mother. In the event that any appendages are missing or are of abnormal length, a diagnosis as to possible deformity is printed out. Organs internal to the fetus may be similarly examined automatically by scanner 42 and computer 24. In more advanced stages of pregnancy, physiological functions such as the heart rate of the fetus may be automatically monitored for abnormal conditions.

The analysis performed by computer 24 on the image from scanner 42 will depend in part on the region of the patient's body being scanned. If a woman's breast or a person's cortex is being monitored for tumorous growths, computer 24 is programmed to separate the tissue image into regions of different textures. The different textured regions are parameterized as to size, shape and location and the derived parameters are compared to values in memory 28 to determine the presence of a tumor. Additional analysis is undertaken to detect lines in an image which may indicate the presence of an organic body.

A similar analysis is undertaken to evaluate a tissue specimen on a slide. The texture and line scanning may be repeated at different magnification levels if, for example, the tissue sample is a slice of an organ wall. On a high magnification level, the texture and line analysis can serve to detect microorganisms in blood.

Memory 28 may store entire images related to different diseases. For example, memory 28 may store images of skin conditions in the event that scanner 42 takes the form of a video camera at a dermatological diagnosis and treatment facility. In a step 54 (FIG. 3), computer 24 compares the image of a patient's skin with previously stored images in memory 28, for example, by breaking down the current image into sections and overlaying the sections with sections of the stored images, at variable magnification levels.

In the event that scanner 42 takes the form of an MRI apparatus or CAT scanner, the images stored in memory 28 are of internal organic structures. In step 54 (FIG. 3), computer 24 compares images of a person's internal organs with previously stored organ images in memory 28. Computer 24 partitions the image from the MRI apparatus or CAT scanner into subareas and overlays the subareas with sections of the stored images, at variable magnification levels.

In a final step 56 (FIG. 3), computer 24 communicates the results of its diagnostic evaluation to a user or patient.

Figure 4:
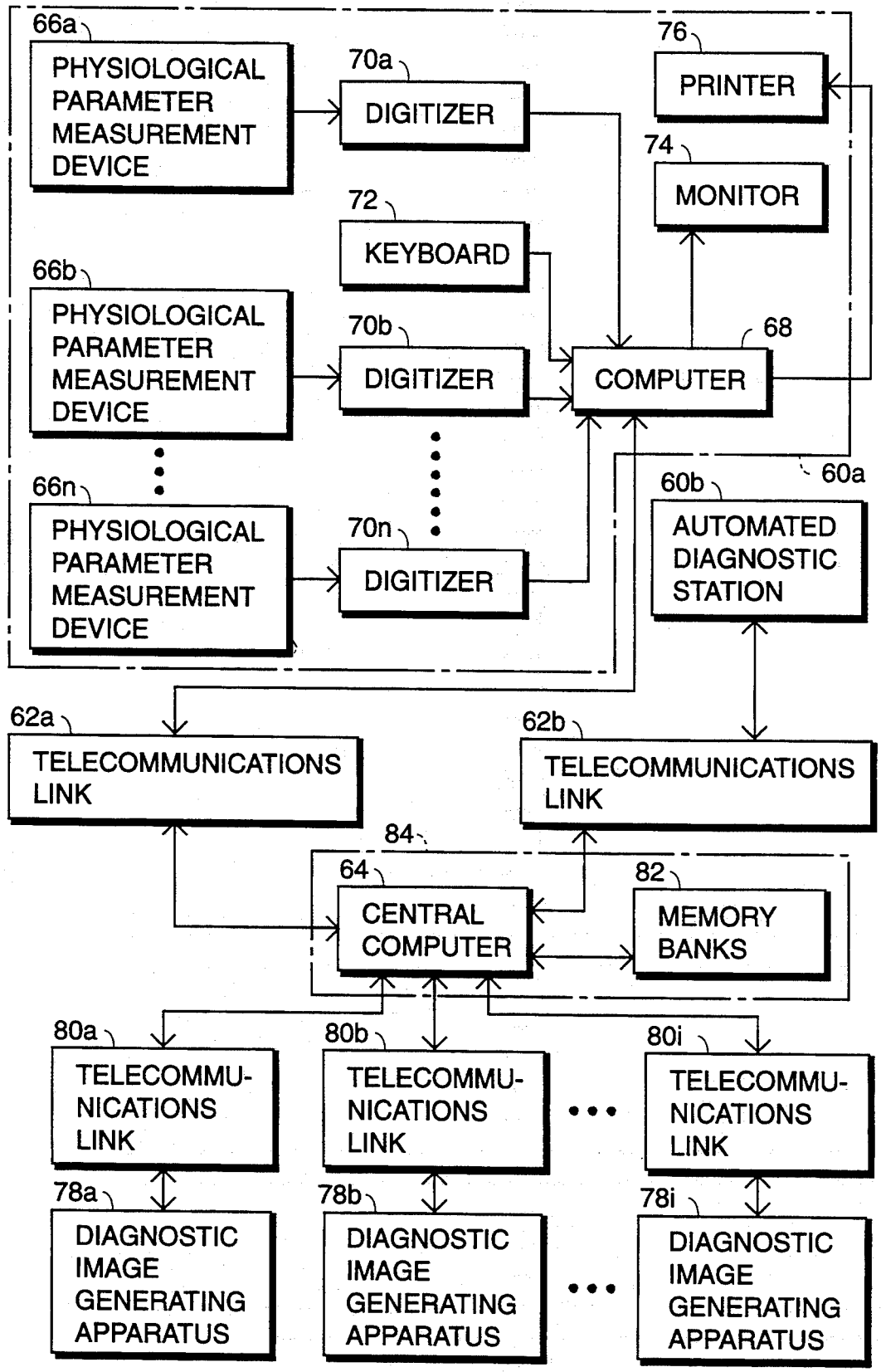
FIG. 4 a block diagram of a further medical diagnostic system, in accordance with the present invention.

As illustrated in FIG. 4, a medical diagnostic system comprises a plurality of remote automated diagnostic stations 60a and 60b connected via respective telecommunications links 62a and 62b to a central computer 64. Each diagnostic station 60a, 60b may take the form shown in FIG. 1, local computer 24 communicating via link 62a, 62b with central computer 64. Alternatively, each diagnostic station 60a, 60b may take the form shown in FIG. 4 and include a respective plurality of monitoring and measuring devices 66a, 66b, . . . 66n operatively connected to a local computer 68 via respective digitizer output units 70a, 70b, . . . 70n. Computer 68 is fed instructions and data from a keyboard 72 and communicates diagnostic results via a monitor 74 or printer 76. As discussed hereinabove with reference to monitoring and measuring device 20 of FIG. 1, each monitoring and measuring device 66a, 66b, . . . 66n is juxtaposable to a patient for collecting individualized medical data about the patient's condition. Monitoring and measuring devices 66a, 66b, . . . 66n may resepctively take the form of an electronic thermometer, an electronic blood pressure gauge, a pulmonary function apparatus, a doppler study apparatus, an EEG machine, an EKG machine, an EMG machine, or a pressure measurement device, etc.

Digitizers 70a, 70b, . . . 70n convert normally analog type signals into coded binary pulses and transmit the resulting digital measurement signals to computer 68. Digitizers 70a, 70b, . . . 70n may be incorporated into the housings or casing (not shown) enclosing all or part of the respective monitoring and measuring devices 66a, 66b, . . . 66n.

Keyboard 72 is used to feed computer 68 information for identifying the patient, for example, the patient's age, sex, weight, and known medical history and conditions. Such medical conditions may include past diseases and genetic predispositions.

As further illustrated in FIG. 4, a plurality of diagnostic image generating apparatuses or scanners 78a, 78b, . . . 78i are also connected to central computer 64 via respective telecommunications links 80a, 80b, . . . 80i. Scanners 78a, 78b, . . . 78i each generate in electrically encoded form a visually readable image of an organic part of the patient. Scanners 78a, 78b, . . . 78i may each take the form of an MRI apparatus, a CAT scanner, an X-ray machine, an ultrasonography apparatus, or a video camera with or without magnification optics for magnifying a sample on a slide.

Because of the enormous quantity of data necessary for storing images, central computer 64 is connected to a bank of memories 82 at a central storage and information processing facility 84. Diagnosis of patient conditions may be undertaken by central computer 64 alone or in cooperation with local computers 24 or 68.

As illustrated in FIG. 5, local computers 24 and 68 transmit information to central computer 64 in data packets or modules each including a first string of binary bits 86 representing the transmitting station 60a, 60b, a second bit string 88 identifying the patient, a bit group 90 designating the parameter which is being transmitted, another bit group 92 coding the particular measured value of the parameter, a set of bits 94 identifying the point on the patient at which the measurement was taken, and another bit set 96 carrying the time and date of the measurement. Other bit codes may be added as needed.

As shown in FIG. 6, a computerized slide scanning system comprises a slide carrier 100 mountable to a microscope stage and a slide positioning device 102 mechanically linked to the slide carrier 100 for shifting the carrier along a path determined by a computer 104. Computer 104 may be connected to an optional transport or feed assembly 106 which delivers a series of slides (not shown) successively to slide carrier 100 and removes the slides after scanning.

Computer 104 is also connected to an optical system 108 for modifying the magnification power thereof between successive slide scanning phases. Light emerging from optical system 108 is focused thereby onto a charge coupled device ("CCD") 110 connected to computer 104 for feeding digitized video images thereto.

Computer 104 performs a line and texture analysis on the digitized image information from CCD 110 to determine the presence of different organic structures and microorganisms. The different textured regions are parameterized as to size, shape and location and the derived parameters are compared to values in a memory to identify microscopic structures. The texture and line scanning is repeated at different magnification levels.

Computer 104 may be connected to a keyboard 112, a printer 114, and a modem 116. Modem 116 forms part of a telecommunications link for connecting computer 104 to a remote data processing unit such as computer 64 in FIG. 4.

Image generating apparatus 42 in FIG. 1 may take the form of the computerized slide scanning system of FIG. 6.

As shown in FIG. 7, a device for measuring a diagnostic parameter and transmitting the measurement over the telephone lines comprises a monitoring and measuring device 118 which may take the form, for example, of an electronic thermometer, an electronic blood pressure gauge, a pulmonary function apparatus, a doppler study apparatus, an EEG machine, an EKG machine, an EMG machine, or a pressure measurement device, etc., or include a plurality of such components. Monitoring and measuring device 118 is connected at an output to a digitizer 120 which in turn is coupled to a modulator 122. Modulator 122 modulates a carrier frequency from a frequency generator 124 with the data arriving from monitoring and measuring device 118 via digitizer 120 and transmits the modulated signal to an electro-acoustic transducer 126 via an amplifier 128. Transducer 126 is removably attachable via a mounting element 130 to the mouthpiece of a telephone handset (not shown) and generates a pressure wave signal which is converted by a microphone in the handset mouthpiece back to an electrical signal for transmission over the telephone lines. Of course, transducer 126 may be omitted and modulator 122 connected directly to a telephone line.

The system of FIG. 7 enables the transmission of specialized medical data directly over the telephone lines to a central computer (e.g. computer 64 in FIG. 4) which utilizes the incoming data to perform a diagnostic evaluation on the patient.

Monitoring and measuring device 118 may include traditional medical instrumentation such as a stethoscope or modern devices such as a CCD.

Figure 8:
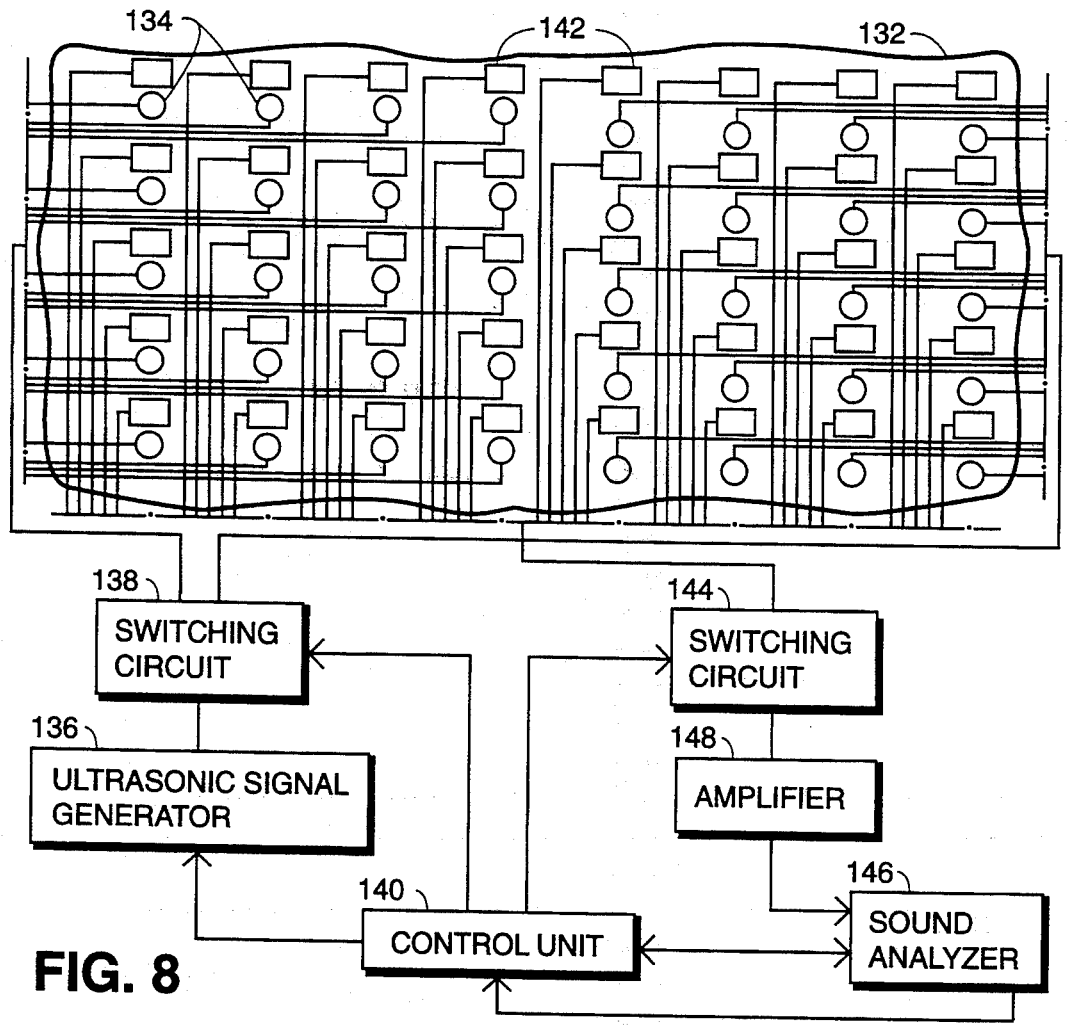
FIG. 8 is a diagram of an ultrasonography device in accordance with the present invention.

FIG. 8 shows an ultrasonographic image generating apparatus which may be used in the medical diagnostic system of FIG. 1 (see reference designation 42) or in the medical diagnostic system of FIG. 4 (see reference designations 78a, 78b, . . . 78i). A flexible web 132 carries a plurality of piezoelectric electroacoustic transducers 134 in a substantially rectangular array. Tranducers 134 are each connectable to an ultrasonic signal generator 136 via a switching circuit 138. Switching circuit 138 is operated by a control unit 140 to connect tranducers 134 to signal generator 136 in a predetermined sequence, depending on the area of a patient's body which is being ultrasonically scanned.

Web 132 also carries a multiplicity of acoustoelectric transducers or sensors 142 also arranged in a substantially rectangular array. Sensors 142 are connected to a switching circuit 144 also operated by control unit 140. An output of switching circuit 144 is connected to a sound analyzer 146 via an amplifier 148.

Web 132 is draped over or placed around a portion of a patient's body which is to be monitored ultrasonically. Control unit 140 then energizes signal generator 136 and operates switching circuit 138 to activate transducers 134 in a predetermined sequence. Depending on the transducer or combination of transducers 134 which are activated, control unit 140 operates switching circuit 144 to connect a predetermined sequence of sensors 142 to sound analyzer 146. Sound analyzer 146 and control unit 140 cofunction to determine three dimensional structural shapes from the echoes detected by sensors 142.

Control unit 140 is connected to ultrasonic signal generator 136 for varying the frequency of the generated signal.

Figure 9:
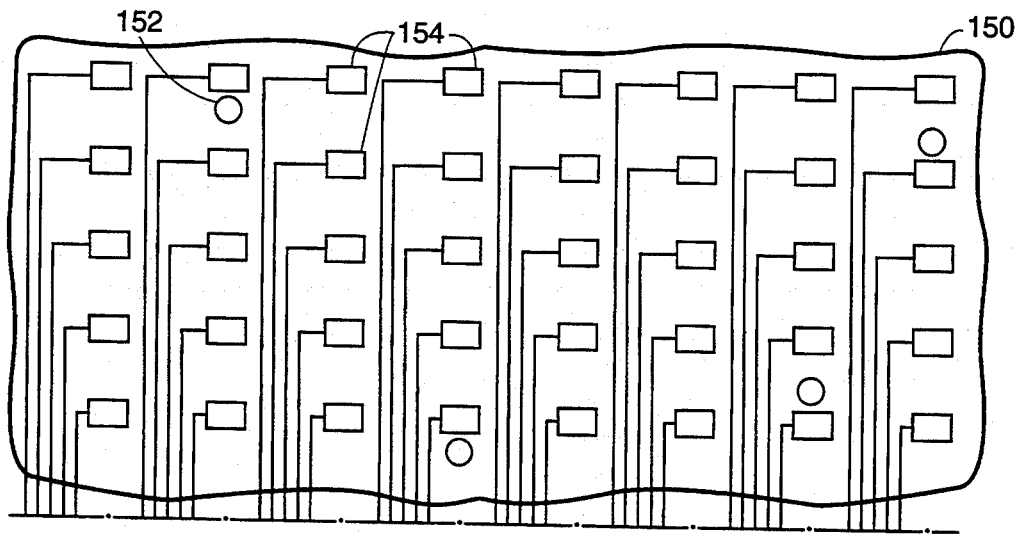
FIG. 9 is a diagram showing a modification of the device of FIG. 8.

FIG. 9 shows a modified ultrasonography web 150 having a limited number of electroacoustic transducers 152 and generally the same number and disposition of sensors 154 as in web 132.

Web 132 or 150 may be substantially smaller than illustrated and may correspondingly carry reduced numbers of transducers 134 and 152 and sensors 142 and 154. Specifically, web 132 or 150, instead of being a sheet large enough to wrap around a torso or arm of a patient, may take a strip-like form which is periodically moved during use to different, predetermined locations on the patient. Control unit 140 and sound analyzer 146 are programmed to detect internal organic structures from the data obtained at the different locations that the web 132 or 150 is juxtaposed to the patient.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical diagnostic method comprising the steps of:
   providing a video camera;
   aiming said video camera at a skin surface of a patient;
   operating said video camera to generate a digitized video signal encoding an image of the skin surface of the patient;
   automatically analyzing said video signal to derive digitized data pertaining to visually detectable characteristics of the skin surface of the patient;
   automatically comparing the digitized data with data stored in an electronic memory to derive a diagnosis as to a skin condition of the patient; and
   communicating the derived diagnosis to a user.

2. The method defined in claim 1 wherein said step of automatically analyzing includes the step of automatically deriving a parameter abstracting information about the image.

3. The method defined in claim 2 wherein said step of analyzing includes the step of automatically determining a percentage of skin covered by an abnormal condition.

4. The method defined in claim 2 wherein said step of analyzing includes the step of determining a range of sizes of individual ulcers on the skin surface of the patient.

5. The method defined in claim 2 wherein said step of analyzing includes the step of determining a range of color variation of the skin surface of the patient.

6. The method defined in claim 1, further comprising the steps of:
   measuring a predetermined physiological parameter of the patient to determine a value for said parameter;
   automatically digitizing the determined value of the physiological parameter,
   said step of comparing including the step of automatically comparing the digitized value of the physiological parameter with data stored in the electronic memory.

7. The method defined in claim 6 wherein said step of measuring includes the step of monitoring a physiological paratmer taken from the group including temperature, blood pressure, pulmonary function, and cardiac function.

8. The method defined in claim 1 wherein said step of comparing includes the step of operating a computer to compare the digitized data with data stored in said memory, further comprising the step of feeding to said computer information pertaining to medical history, past diseases and genetic predispositions of the patient.

9. A medical diagnostic method comprising the steps of:
   scanning the patient to generate a digitized electrical signal encoding an image of an organic part of the patient;
   automatically analyzing said video signal to derive digitized data pertaining to structural characteristics of the organic part of the patient;
   measuring a predetermined physiological parameter of the patient to determine a value for said parameter;
   automatically digitizing the determined value of the physiological parameter;
   automatically comparing the digitized data and the digitized value of the physiological parameter with data stored in an electronic memory to derive a diagnosis as to the patient's condition; and
   communicating the derived diagnosis to a user,
   said step of scanning including the steps of aiming a video camera at a skin surface of the patient and operating said video camera to generate in electrically encoded form a visually readable image of the skin surface of the patient, said electrical signal being a video signal, said visually readable image being encoded in said video signal.

10. The method defined in claim 9 wherein said step of measuring includes the step of monitoring a physiological paratmer taken from the group including temperature, blood pressure, pulmonary function, and cardiac function.

11. The method defined in claim 9 wherein said step of comparing includes the step of operating a computer to compare the digitized data and the digitized value of the physiological parameter with data stored in said memory, further comprising the step of feeding to said computer information pertaining to medical history, past diseases and genetic predispositions of the patient.

12. A medical diagnostic system comprising:
   scanning means juxtaposable to a patient for collecting image type data about the patient and for generating a first digitized electrical signal encoding said image type data;
   monitoring means juxtaposable to the patient for collecting data about a physiological characteristic of the patient and for generating a second digitized electrical signal encoding said data about said physiological characteristic;
   memory means for storing medical data for a multiplicity of previously diagnosed medical conditions;
   computing means operatively connected to said memory means, said scanning means, and said monitoring means for comparing data encoded in said first electrical signal and in said second electrical signal with the data stored in said memory means and for deriving a diagnosis as to the patient's condition; and
   output means operatively connected to said computing means for communicating the derived diagnosis to a user.

13. The system defined in claim 12 wherein said scanning means includes a device taken from the group consisting of an NMI apparatus, a CAT scanner, an X-ray machine, an ultrasonography apparatus, and a video camera.

14. The system defined in claim 12 wherein said monitoring means includes a device taken from the group including an electronic thermometer, an electronic blood pressure gauge, a pulmonary function apparatus, a doppler study apparatus, an EEG machine, an EKG machine, and an EMG machine.

* * * * *